United States Patent
Amalric et al.

(10) Patent No.: US 8,722,069 B2
(45) Date of Patent: May 13, 2014

(54) OIL-IN-WATER EMULSION HAVING IMPROVED SENSORY PROPERTIES

(75) Inventors: Chantal Amalric, Blan (FR); Juanshu Shen, Castres (FR); Jerome Guilbot, Castres (FR); Herve Rolland, Castres (FR); Agnes Gorce, Marseilles (FR); Sebastien Kerverdo, Vincennes (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 0 days.

(21) Appl. No.: 13/383,425

(22) PCT Filed: Jul. 22, 2010

(86) PCT No.: PCT/FR2010/051556
§ 371 (c)(1),
(2), (4) Date: Jan. 11, 2012

(87) PCT Pub. No.: WO2011/015759
PCT Pub. Date: Feb. 10, 2011

(65) Prior Publication Data
US 2012/0114573 A1    May 10, 2012

(30) Foreign Application Priority Data
Jul. 27, 2009  (FR) .................................. 09 55247

(51) Int. Cl.
*A61K 8/00* (2006.01)
*A61K 8/02* (2006.01)
*A61K 8/06* (2006.01)

(52) U.S. Cl.
CPC .. *A61K 8/062* (2013.01); *A61K 8/06* (2013.01)
USPC .......................................... 424/401; 424/59

(58) Field of Classification Search
CPC .................................................... A61K 8/062
See application file for complete search history.

(56) References Cited

U.S. PATENT DOCUMENTS

| | | | |
|---|---|---|---|
| 6,231,837 B1 * | 5/2001 | Stroud et al. | 424/59 |
| 6,348,202 B1 | 2/2002 | Wadle | |
| 6,353,034 B1 * | 3/2002 | Amalric et al. | 516/72 |
| 6,358,500 B1 | 3/2002 | Simon | |
| 2001/0008935 A1 * | 7/2001 | Milius et al. | 536/18.6 |
| 2002/0065328 A1 * | 5/2002 | Dederen et al. | 516/9 |

FOREIGN PATENT DOCUMENTS

| | | |
|---|---|---|
| DE | 197 30 423 | 12/1998 |
| EP | 0 958 856 | 11/1999 |
| EP | 958856 A1 * | 11/1999 |
| FR | 2 803 537 | 7/2001 |
| FR | 2 830 464 | 4/2003 |
| WO | 92/06778 | 4/1992 |
| WO | 94/01073 | 1/1994 |
| WO | 95/13863 | 5/1995 |
| WO | 96/37285 | 11/1996 |
| WO | 00/56438 | 9/2000 |
| WO | 01/58578 | 8/2001 |

OTHER PUBLICATIONS

French Search Report dated Apr. 30, 2010, corresponding to the Priority Application No. 0955247.

* cited by examiner

*Primary Examiner* — Susan Tran
(74) *Attorney, Agent, or Firm* — Young & Thompson

(57) ABSTRACT

An oil-in-water emulsion includes, for 100 wt % thereof: a) 0.1 to 10 wt % of an emulsifying system including, for 100 wt % thereof: (i) 5 to 95 wt % of the mixture of the reaction products of a reducing sugar and 1,12-octadecanediol essentially consisting of hydroxyl-octadecyl polyglycosides of formula (I): HO—R—O-$(G)_n$-H (I) and of polyglycosyl octadecyl polyglycosides of formula (II): H-$(G)_m$-O—R—O-$(G)_p$-H (II), where, in formulas (I) and (II), G is the remainder of the reducing sugar and R is the divalent radical octadecanediyl-1,12, and where n, m and p, identical or different, each are, independently of each other, a decimal number between 1 and 5; (ii) 95 to 5 wt % of 1,12-octadecanediol; b) 0.01 to 5 wt % of at least one thickening and/or gelling agent; c) 10 to 50 wt % of an oil phase; and d) 89.89 to 35 wt % of an aqueous phase.

6 Claims, No Drawings

OIL-IN-WATER EMULSION HAVING IMPROVED SENSORY PROPERTIES

The present invention relates to novel compositions in the form of oil-in-water emulsions, and the methods of preparation thereof.

The invention preferably finds application in the cosmetic and dermocosmetic field, in the dermopharmaceutical and pharmaceutical field, notably for use in the care, protection and cleaning of the skin, hair and scalp, but also in the field of the textile industry, for example for the treatment of woven or knitted, synthetic or natural textile fibers, or in the field of the papermaking industry, for example for the manufacture of paper for sanitary or household use.

In the development of formulations intended for treating and/or protecting the skin and/or the mucous membranes and/or the scalp, and generally for body care products, the sensory properties constitute an important criterion for their commercial success. In fact, the end user's choice is based as much on sensory criteria and criteria of immediate well-being as on technical performance criteria provided by the cosmetic formulations when applied on the skin. Moreover, the use of ingredients of natural origin for preparing cosmetic formulations is also an element of the commercial success of these products as it means that labels can be obtained from professional bodies, certifying their natural origin. In the preparation of these cosmetic formulations, it is possible to use fats of vegetable origin as fatty phases, thickeners and/or gelling agents and/or stabilizers of natural origin, surfactants prepared from raw materials of vegetable origin as emulsifiers. Among the surfactants used as emulsifiers and prepared from raw materials of vegetable origin, formulators commonly use esters of glycerol and of fatty acids of vegetable origin, such as glycerol stearate, soaps such as sodium stearate, surfactants derived from sugars and fatty acids of vegetable origin, such as sucrose fatty esters, as well as surfactants derived from sugars and fatty alcohols of vegetable origin that were developed more than about twenty years ago and whose commercial success no longer requires further demonstration. These emulsifiers consist of a mixture of alkyl polyglycosides and fatty alcohols and are marketed either in solid form, as flakes or beads, or in a form that is liquid at room temperature depending on the fatty alcohols used. They are described for example in the international applications published under numbers WO 92/06778, WO 95/13863, WO 96/37285 or WO 00/56438 or in the French patent application published under number FR 2 830 464.

The French patent application published under number FR 2 803 537 discloses more particularly compositions comprising 5 to 95 parts by weight of a mixture of alkyl polyglycosides consisting of the reaction products of a saccharide and of 1,12-octadecanediol, and from 95 to 5 parts by weight of 1,12-octadecanediol. They can be used for preparing emulsions that are opaque and stable, suitable for preparing foaming cosmetic formulations. This publication also discloses a cosmetic composition used as a foaming makeup-removal milk comprising, per 100% of its weight, 4 wt. % of a mixture of 1,12-octadecanediol and alkyl polyglycosides whose alkyl chain consists of the 12-hydroxyoctadecyloxy radical, 4 wt. % of jojoba oil, 3 wt. % of a thickener based on acrylic copolymers marketed under the name CAPIGEL™98, 7 wt. % of lauryl ether sodium sulfate and the remainder to 100 wt. % being water. Jojoba oil is a mixture of esters; each molecule is composed of a linear fatty acid and a linear fatty alcohol, each comprising 18 to 22 carbon atoms, joined together by an ester bond (D. J. Understander, E. A. Oelke, A. R. Kaminski, J. D. Doll, S. M. Combs, and C. V. Hanson, *"Jojoba"* in *Alternative Field Crops Manual*, 1990). The emulsifying compositions described in FR 2 803 537 are suitable for foaming cosmetic compositions, and can improve the stability and opacity, a visual property, of said compositions.

The international publication WO 95/13863 discloses a concentrate comprising an emulsifying mixture of alkyl polyglycosides and fatty alcohols intended for preparing emulsions with improved stability and of endowing said emulsion with a nacreous effect, namely a visual effect consisting of endowing the cosmetic composition with an iridescent, moiré, metallized or opacifying effect. The stability that this emulsifying and luster-producing concentrate imparts can enable the formulator to avoid the use of stabilizers such as thickening polymers usually employed for perfecting the stability of emulsions.

The publication U.S. Pat. No. 6,348,202 B1 discloses the preparation of cosmetic self-tanning compositions comprising dihydroxyacetone and nonionic emulsifiers, said nonionic emulsifiers consisting of a mixture of alkyl and/or alkenyl oligoglycosides and poly-12-hydroxystearate polyols. The use of said nonionic emulsifiers can endow the self-tanning cosmetic composition with improved stability and can prevent chemical decomposition of the dihydroxyacetone during high-temperature storage of the self-tanning cosmetic composition.

However, when cosmetic formulations comprising fats of vegetable origin and/or thickeners and/or gelling agents and/or stabilizers of natural origin, and/or emulsifiers derived from sugars and fatty alcohols of vegetable origin, and/or emulsifiers derived from sugars and fatty acid of vegetable origin, and/or emulsifiers based on esters of fatty acids of vegetable origin and of glycerol, are applied on the skin, the sensory results are unsatisfactory.

The sensory properties of a cosmetic formulation for body care are characterized by several criteria, among which we may mention the sensation of softness for the user during application of the composition on the skin, the consistency of the composition and the so-called "soaping" phenomenon. The consistency of a cosmetic formulation is characterized by its resistance to flow. It is determined empirically, by visual observation of the flow of the cosmetic formulation under the effect of gravity and/or by measuring a maximum force of compression applied by means of a texturometer equipped with a measuring probe and connected to data processing software. The so-called "soaping" phenomenon mentioned above is characterized by the appearance of a whitish film on the skin, during application of the formulation on the skin. This criterion is evaluated by visual observation of its existence and/or of how quickly it appears. It can be reduced by incorporating additives in cosmetic formulations, such as silicone oils as described by E. W. Flick in the reference work "Cosmetic additives—an industrial guide", William Andrew Publishing/Noyes, 1991.

It is also disclosed in international publication WO 94/01073 that the preparation of formulations intended for treating and/or protecting the skin that are in the form of triple emulsions and comprise silicone polymers having a polyethoxylated and/or polypropoxylated chain made it possible to avoid this "soaping" phenomenon described above.

The European patent application published under number EP 0 958 856 A1 also describes formulations that are in the form of water-in-oil-in-water triple emulsions and are characterized by the presence of at least one partially or fully crosslinked organopolysiloxane elastomer having a polyethoxylated and/or polypropoxylated chain, which do not display the "soaping" phenomenon during their application on the skin.

However, these technical solutions have the drawback that they introduce constituent ingredients of the cosmetic formulations that are not of natural origin.

The inventors therefore tried to develop novel compositions comprising ingredients of natural origin and displaying improved sensory properties, i.e. compositions:

which remain homogeneous during storage at room temperature after a minimum time of one month, which are characterized by a softness index, the protocol for which is described in paragraph II-3 of the experimental section of the present account, above a value of 7.0, which are evaluated as satisfactory according to the criterion of consistency, prior to application on the skin, by a suitably trained panel of 11 people according to the operating conditions of the test for sensory analysis, the protocol of which is described in paragraph II-2 of the experimental section of the present account, which are evaluated as "non-soaping" during the phase of application on the skin by a suitably trained panel of 11 people according to the operating conditions of the test for sensory analysis, the protocol of which is described in paragraph II-1 of the experimental section of the present account.

Therefore, according to a first aspect, the invention relates to a composition that is in the form of an oil-in-water emulsion comprising per 100% of its weight:

a)—From 0.1 to 10 wt. % of an emulsifying system (A) consisting per 100% of its weight of:

(i)—From 5 to 95 wt. % of the mixture of reaction products of a reducing sugar and of 1,12-octadecanediol constituted essentially of hydroxyoctadecyl polyglycosides of formula (I):

HO—R—O-(G)$_n$-H    (I)

and of polyglycosyloctadecyl polyglycosides of formula (II):

H-(G)$_m$-O—R—O-(G)$_p$-H    (II), where, in formulas (I) and (II), G represents the residue of said reducing sugar and R represents the 1,12-octadecanediyl divalent radical and in which n, m and p, which may be identical or different, each represent, independently of one another, a decimal number between 1 and 5;

(ii)—From 95 to 5 wt. % of 1,12-octadecanediol;

b)—From 0.01 to 5 wt. % of at least one thickener and/or gelling agent selected from thickeners and/or gelling agents of natural origin;

c)—From 10 to 50 wt. % of a fatty phase (P2) consisting of one or more vegetable oils based on monoglycerides and/or diglycerides and/or triglycerides; and d)—From 89.89 to 35 wt. % of a cosmetically acceptable aqueous phase (P1).

In the definition of formula (I) as defined above, n is a decimal number, which represents the average degree of polymerization of the residue G. When n is an integer, (G)$_n$ is the polymer residue of rank n of the residue G. When n is a decimal number, formula (I) represents a mixture of compounds:

$a_1$ HO—R—O-G-H+$a_2$ HO—R—O-(G)$_2$-H+$a_3$ HO—R—O-(G)$_3$-H+ . . . +$a_q$ HO—R—O-(G)$_q$-H with q representing an integer between 1 and 5 and in molar proportions $a_1$, $a_2$, $a_3$, . . . $a_q$ such that:

$$\sum_{q=5}^{q=1} a_q = 1; a_1 > 0$$

In the definition of formula (II) as defined above, m and p are decimal numbers, which represent the average degree of polymerization of the residue G. When m is an integer, (G)$_m$ represents the polymer residue of rank m of the residue G. When p is an integer, (G)$_p$ represents the polymer residue of rank p of the residue G. When m and p are decimal numbers, formula (II) represents a mixture of compounds:

$b_1$ H-G-O—R—O-G-H+$b_2$ H-G-O—R—O-(G)$_2$-H+$b_3$ H-G-O—R—O-(G)$_3$-H+ . . . +bq H-G-O—R—O-(G)$_q$-H+$c_1$ H-(G)$_2$-O—R—O-G-H+$c_2$ H-(G)$_2$-O—R—O-(G)$_2$-H+$c_3$ H-(G)$_2$-O—R—O-(G)$_3$-H+ . . . cq H-(G)$_2$-O—R—O-(G)$_q$-H+ . . . , $d_1$ H-(G)$_3$-O—R—O-G-H+$d_2$ H-(G)$_3$-O—R—O-(G)$_2$-H+$d_3$ H-(G)$_3$-O—R—O-(G)$_3$-H+ . . . dq H-(G)$_3$-O—R—O-(G)$_q$-H+$e_1$ H-(G)$_4$-O—R—O-G-H+$e_2$ H-(G)$_4$-O—R—O-(G)$_2$-H+$e_3$ H-(G)$_4$-O—R—O-(G)$_3$-H+ . . . eq H-(G)$_4$-O—R—O-(G)$_q$-H+$f_1$ H-(G)$_5$-O—R—O-G-H+$f_2$ H-(G)$_5$-O—R—O-(G)$_2$-H+$f_3$ H-(G)$_5$-O—R—O-(G)$_3$-H+ . . . fq H-(G)$_5$-O—R—O-(G)$_q$-H, with q representing an integer between 1 and 5 and in molar proportions such that:

$$\sum_{q=5}^{q=1} b_q + \sum_{q=5}^{q=1} c_q + \sum_{q=5}^{q=1} d_q + \sum_{q=5}^{q=1} e_q + \sum_{q=5}^{q=1} f_q = 1 \text{ with } b_1 > 0$$

According to a particular aspect of the present invention, in formulas (I) and (II), n, m and p are, independently of one another, between 1.05 and 5, and more particularly between 1.05 and 2.

"Reducing sugar" denotes, in formulas (I) and (II), saccharide derivatives whose structures do not have a glycosidic bond established between an anomeric carbon and the oxygen of an acetal group as defined in the reference work: "Biochemistry", Daniel Voet/Judith G. Voet, p. 250, John Wiley & Sons, 1990. The oligomeric structures (G)n, (G)$_m$ and (G)$_p$ can be in any form of isomerism, whether it is optical isomerism, geometric isomerism or positional isomerism; they can also represent a mixture of isomers.

In formula (I) as defined above, the group HO—R—O is bound to G by the anomeric carbon of the saccharide residue, so as to form an acetal function.

In formula (II) as defined above, the group O—R—O is bound to each residue G by the anomeric carbon of each saccharide residue, so as to form two separate acetal functions.

According to a particular aspect of the present invention, in the definition of the compounds of formulas (I) and (II), G represents a reducing sugar selected from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose and more particularly a reducing sugar selected from glucose, xylose or arabinose.

Said emulsifying system (A) can be prepared by simple mixing of the compounds of formula (I), of the compounds of formula (II) and of 1,12-octadecanediol in desired predetermined proportions.

Said emulsifying system (A) can also be prepared according to a method comprising:

A step a) of reaction of the reducing sugar G with a stoichiometric excess of 1,12-octadecanediol in the presence of an acid catalytic system.

In said method of preparation of the emulsifying system (A), step a) is generally carried out in a reactor, controlling the stoichiometric ratio between the two reactants, and with mechanical stirring in predetermined conditions of temperature and partial vacuum, for example at a temperature between 70° C. and 130° C. and under a partial vacuum between 300 mbar (3 10$^4$ Pa) and 20 mbar (2 10$^3$ Pa).

"Acid catalytic system" denotes strong acids such as sulfuric acid, hydrochloric acid, phosphoric acid, nitric acid, hypophosphorous acid, methanesulfonic acid, para-toluene sulfonic acid, trifluoromethane sulfonic acid, or acidic ion exchange resins.

Said emulsifying system (A) can also be prepared according to a variant of the method as described above, comprising:

A step a1) of reaction of a reducing sugar G with an alcohol of formula (III):

in which $R_3$ represents a linear aliphatic radical having from 1 to 4 carbon atoms, and more particularly with butanol, in the presence of an acid catalytic system, to form the acetal of formula (IV):

in which p represents a decimal number between 1 and 5.

A step b) of trans-acetalization of the acetal of formula (IV) obtained in step a1), by adding an excess of 1,12-octadecanediol with vacuum distillation of the alcohol of formula (III) formed in situ.

Step a1) of the variant of the method as defined above is more particularly carried out at a temperature between 90° C. and 105° C., under partial vacuum, and it is often accompanied by concomitant removal of the water formed during the reaction. The catalytic system employed in this step a1) is more particularly that as described for application of the method of preparation from which said variant is derived.

The method and the variant thereof can, if necessary or if desired, be supplemented with operations of neutralization, filtration and bleaching.

The 1,12-octadecanediol used for preparation of the emulsifying system (A) included in the composition of the invention is a diol resulting from hydrogenation of fatty acids of castor oil. It is notably marketed by the company Cognis under the name Speziol™ C18/2.

"Thickener and/or gelling agent of natural origin" denotes chemical substances for thickening aqueous phases, the raw materials required for their preparation being plants, algae, minerals, and chemical substances that are obtained by fermentive action of at least one bacterium and of at least one hydrocarbon substrate, where the raw materials required for preparation thereof are plants or algae.

Among thickeners and/or gelling agents of natural origin, we may mention polysaccharides and proteins that are topically acceptable and are usually employed in this sphere of activity, for example acacia gum, karaya gum, ghatti gum, sclerotium gum, guar gum, carob, pectin, fenugreek, carraghenates, alginates, galactomannans, cellulose and derivatives thereof, starch and derivatives thereof, xanthan gum, aluminum silicates, magnesium silicates.

According to a particular aspect, the composition according to the present invention comprises, per 100% of its weight, between 0.01 and 5 wt. % of at least one thickener and/or gelling agent selected from thickeners and/or gelling agents of natural origin, and more particularly between 0.1 and 5 wt. %.

According to another particular aspect, the composition according to the present invention comprises at least one thickener and/or gelling agent of natural origin selected from the elements of a group consisting of xanthan gum, acacia gum, guar gum, pectin, carob, fenugreek, carraghenates, alginates and galactomannans.

"Oils of vegetable origin based on monoglycerides and/or diglycerides and/or triglycerides" means the chemical substances comprising monoglycerides of formula (A1) and/or of formula (A'1), and/or diglycerides of formula (A2) and/or of formula (A'2), and/or triglycerides of formula (A3) whose raw materials required for preparation thereof are plants:

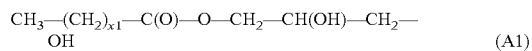

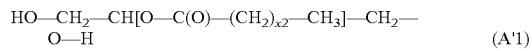

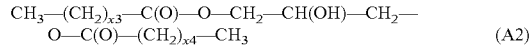

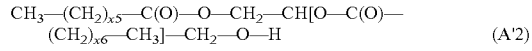

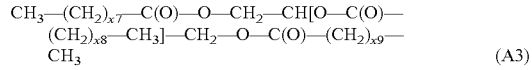

where x1, x2, x3, x4, x5, x6, x7, x8 and x9, which may be identical or different, represent an integer between 7 and 23.

Among the oils of vegetable origin based on monoglycerides and/or ditriglycerides and/or triglycerides as defined above, we may mention for example sweet almond oil, copra oil, castor oil, olive oil, colza oil, peanut oil, sunflower oil, wheat germ oil, maize germ oil, soybean oil, cottonseed oil, alfalfa oil, poppy oil, pumpkin oil, pastel woad oil, borage oil, evening primrose oil, millet oil, barley oil, rye oil, safflower oil, candlenut oil, passionflower oil, hazelnut oil, palm oil, shea butter, apricot kernel oil, calophyllum oil, sysymbrium oil, avocado oil, calendula oil, hemp oil, oils obtained from flowers, oils obtained from vegetables, triglycerides obtained by an esterification reaction between a fatty acid of vegetable origin and glycerol for example the caprylic capric triglyceride marketed under the name DUB MCT by the company STEARINERIE DUBOIS, the triglycerides obtained by an esterification reaction between fatty acids having seven carbon atoms and glycerol marketed under the name DUB THG by the company STEARINERIE DUBOIS, the triglycerides obtained by an esterification reaction between fatty acids having 22 carbon atoms and glycerol marketed under the name SYNCHROWAX HRC by the company CRODA.

The expression "cosmetically acceptable" used in the definition of the aqueous phase (P1) of the composition that is in the form of an oil-in-water emulsion according to the present invention, means according to the directive of the Council of the European Economic Community No. 76/768/EEC of 27 Jul. 1976 as amended by directive No. 93/35/EEC of 14 Jun. 1993, that said aqueous phase (P1) comprises water and any substance or preparation intended to be brought into contact with the various parts of the human body (epidermis, bristle and hair system, nails, lips and genital organs) or with the teeth and the oral mucosae for the purpose, exclusively and principally, of cleaning them, of perfuming them, of modifying their appearance and/or of correcting body odors and/or of protecting them or of maintaining them in good condition.

A cosmetically acceptable aqueous phase (P1) included in these compositions that is in the form of an oil-in-water emulsion according to the present invention contains water, and can conventionally contain one or more cosmetically acceptable organic solvents, a mixture of water and of one or more cosmetically acceptable organic solvents. The cosmetically acceptable solvents can more particularly be selected from polyhydric alcohols for example glycerol, diglycerol, oligomers of glycerol, ethylene glycol, propylene glycol, butylene glycol, hexylene glycol, diethylene glycol, xylitol, erythritol, sorbitol, or water-soluble alcohols such as ethanol, isopropanol or butanol.

According to another more particular aspect, the composition according to the present invention comprises, per 100% of its weight, from 0.5 to 10 wt. % of dihydroxyacetone.

Dihydroxyacetone is a product commonly used in cosmetics as an agent for artificial bronzing and/or tanning of the skin which makes it possible to obtain a bronzing or tanning effect of more or less similar appearance to that which can result from prolonged exposure to the sun or under an ultraviolet lamp. The composition that is in the form of an oil-in-water emulsion comprising, per 100% of its weight, from 0.5 to 10 wt. % of dihydroxyacetone, according to the present invention, can also be combined with other agents for bronzing and/or tanning of the skin, among which we may mention the mono- or polycarbonylated compounds, for example isatin, alloxan, ninhydrin, glyceraldehyde, mesotartaric aldehyde, glutaraldehyde, erythrulose.

In general, the composition according to the present invention also comprises excipients and/or active principles usually employed in the area of cosmetic, dermocosmetic, pharmaceutical or dermopharmaceutical formulations, such as co-emulsifying surfactants, such as detergent surfactants, such as stabilizers, film-forming compounds, luster agents, superfatting agents, thickening and/or gelling surfactants, sequestering agents, hydrotropic agents, plasticizers, superfatting agents, antioxidants, fats of natural origin, preservatives, active principles intended to provide a treating action on the skin or on the hair, sun filters, mineral fillers or pigments, particles imparting a visual effect or intended for encapsulation of active ingredients, exfoliating particles, texture agents.

Among the active principles that can be included in the composition according to the present invention, we may mention active principles having a lightening or depigmenting action, a hydrating action, a lifting action, a soothing or relaxing action, an anti-inflammatory action, a slimming action, a lipolytic action, a draining action, a detoxifying action, an energizing action, a decontracting action, a stimulating action, an emollient action, a neuromodulator action, a protective action, a purifying action, seboregulatory action, action stopping hair loss, an antiaging action, a firming, restructuring, antiradical, or antioxidant action. Said active principles are for example N-acylated proteins, N-acylated peptides for example MATRIXIL™, N-acylated amino acids being in the form of acids and/or salts for example the N-(ω-undecylenoyl) phenylalanine marketed by the company SEPPIC under the name SEPIWHITE™MSH, the octanoylglycine marketed by the company SEPPIC under the name LIPACIDE™C8G, the undecylenoylglycine marketed by the company SEPPIC under the name LIPACIDE™UG, the partial hydrolyzates of N-acylated proteins, amino acids, peptides, the full hydrolyzates of proteins, fat-soluble vitamins, derivatives of fat-soluble vitamins for example retinol, vitamin E and derivatives thereof, water-soluble and/or water-dispersible vitamins for example vitamin C and derivatives thereof, magnesium ascorbyl phosphate and derivatives thereof, ascorbyl glucoside, phytic acid, fruit acids, aqueous or aqueous-alcoholic or aqueous-glycolic extracts of polyphenols, of quinoa, of parsnip, of potentilla, of grape, of wine, extracts of olives, extracts of marc, polyols (for example, glycerol or butylene glycol), derivatives of milk, or the various components in the composition of NMF (natural moisturizing factor) for example urea, pyrrolidone carboxylic acid or derivatives of said acid, amino acids, mineral salts, sugars or derivatives of sugars, polysaccharides or derivatives thereof, hydroxy acids for example lactic acid, aqueous or aqueous-alcoholic or aqueous-glycolic plant extracts, such as plant extracts rich in tannins, plant extracts rich in isoflavones or plant extracts rich in terpenes, extracts of fresh-water or marine algae, marine extracts in general such as coral, bacterial extracts; minerals such as GIVOBIO™, derivatives of calcium, of magnesium, of copper, of cobalt, of zinc, of lithium, or of manganese, salts of silver or of gold; active ingredients having an energizing or stimulating property such as SEPITONIC™ M3 or Physiogényl™; self-tanning active ingredients for example dihydroxyacetone and erythrulose; active ingredients for hydrating or restructuring the epidermis for example AQUAXYL™, lipids in general, lipids such as ceramides or phospholipids, active ingredients having a slimming or lipolytic action such as caffeine or derivatives thereof, panthenol and derivatives thereof such as SEPICAP™ MP, antiaging active ingredients such as SEPILIFT™ DPHP, LIPACIDE™ PVB, active ingredients increasing the synthesis of components of the extracellular matrix for example collagen, elastins, glycosaminoglycans, active ingredients acting favorably on cellular communication: chemical such as cytokines or physical such as integrins, active ingredients creating a sensation of "heat" on the skin such as activators of the cutaneous microcirculation (for example nicotinates) or products creating a sensation of "freshness" on the skin (for example menthol and derivatives thereof); honey; floral water, for example water of young barley shoots.

As examples of texture agents optionally present in the composition according to the present invention, we may mention N-acylated derivatives of amino acids, for example lauroyl lysine marketed under the name AMINOHOPE™LL by the company AJINOMOTO, octenyl starch succinate marketed under the name DRYFLO™ by the company NATIONAL STARCH, myristyl polyglucoside marketed by SEPPIC under the name MONTANOV 14, cellulose fibers, cotton fibers, chitosan fibers, talc, sericite, mica.

As examples of opacifiers and/or luster agents optionally present in the composition according to the present invention, we may mention sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, fatty alcohols.

As examples of thickening and/or gelling surfactants optionally present in the composition according to the present invention, we may mention:
    fatty esters of alkyl polyglycosides optionally alkoxylated, and quite particularly the ethoxylated esters of methylpolyglucoside such as PEG 120 methyl glucose trioleate and PEG 120 methyl glucose dioleate marketed respectively under the names GLUCAMATE™ LT and GLUMATE™ DOE120;
    alkoxylated fatty esters such as the PEG 150 pentaerythrytyl tetrastearate marketed under the name CROTHIX™ DS53, the PEG 55 propylene glycol oleate marketed under the name ANTIL™ 141;
    the fatty-chain polyalkylene glycol carbamates such as the PPG 14 laureth isophoryl dicarbamate marketed under the name ELFACOS™ T211, the PPG 14 palmeth 60 hexyl dicarbamate marketed under the name ELFACOS™ GT2125.

As examples of co-emulsifying surfactants optionally present in the composition according to the present invention, we may mention nonionic surfactants, anionic surfactants, cationic surfactants.

As examples of nonionic co-emulsifying surfactants optionally present in the composition according to the present invention, we may mention the esters of fatty acids and of sorbitol, for example the products marketed under the names MONTANE™80 and MONTANE™85 and MONTANE™60 by the company SEPPIC; the alkyl polyglycosides; the compositions of alkyl polyglycosides and of linear or branched fatty alcohols, for example the compositions marketed under the names MONTANOV™ and FLUIDANOV™ by the company SEPPIC; esters of fatty acid and of polyglycerol, for example the products marketed under the designation ISOLAN™ GI34 by the company BASF and PLUROL™ DIISOSTEARIQUE by the company GATTEFOSSE; ethoxylated castor oil and ethoxylated hydrogenated castor oil for example the product marketed under the designation SIMULSOL™ 989 by the company SEPPIC; the compositions comprising glycerol stearate and ethoxylated stearic acid between 5 moles and 150 moles of ethylene oxide, for example the composition comprising ethoxylated stearic acid with 135 moles of ethylene oxide and of glycerol stearate marketed under the name SIMULSOL 165 by the company SEPPIC; the polyhydroxystearates of polyglycol or of polyglycerol for example the products designated HYPERMER™ B246, ARLACEL™P135 marketed by the company UNIQEMA, the product designated DEHYMULS™ PGPH marketed by the company COGNIS, the product designated DECAGLYN™ 5HS marketed by the company NIKKO; the polyethylene glycol-alkylglycol copolymers such as the PEG-45 dodecylglycol copolymer such as the product marketed under the designation ELFACOS™ ST 9 by the company AKZO; the ethoxylated sorbitan esters for example the products marketed under the designation MONTANOX™ by the company SEPPIC; the mannitan esters; the ethoxylated mannitan esters; the sucrose esters; the methylglucoside esters.

As examples of anionic co-emulsifying surfactants optionally present in the composition according to the present invention, we may mention decylphosphate, cetylphosphate marketed under the name AMPHISOL™ by the company DSM, glyceryl stearate citrate; cetearyl sulfate; the composition arachidyl/behenyl phosphates and arachidyl/behenyl alcohols marketed under the name SENSANOV™WR by the company SEPPIC; soaps for example sodium stearate or triethanolammonium stearate, the salified lipoamino acids for example stearoyl glutamate.

As examples of cationic co-emulsifying surfactants optionally present in the composition according to the present invention, we may mention aminoxides, quaternium-82 and the surfactants described in patent application WO96/00719 and mainly those whose fatty chain comprises at least 16 carbon atoms.

As examples of detergent surfactants optionally present in the composition according to the present invention, we may mention anionic detergent surfactants, cationic detergent surfactants, amphoteric detergent surfactants, nonionic detergent surfactants.

Among the anionic detergent surfactants optionally present in the composition according to the present invention, we may mention in particular the salts of alkali metals, salts of alkaline-earth metals, ammonium salts, salts of amines, salts of aminoalcohols of the following compounds: alkyl ether sulfates, alkylsulfates, alkylamidoether sulfates, alkarylpolyether sulfates, monoglyceride sulfates, alpha-olefin sulfonates, paraffin sulfonates, alkylphosphates, alkyl ether phosphates, alkylsulfonates, alkylamide sulfonates, alkarylsulfonates, alkylcarboxylates, alkylsulfosuccinates, alkyl ether sulfosuccinates, alkylamidesulfosuccinates, alkylsulfoacetates, alkylsarcosinates, acylisethionates, N-acyltaurates, acyllactylates. Among the anionic surfactants, we may also mention lipoamino acids, lipoproteins, lipopeptides, derivatives of lipoproteins, derivatives of proteins, salts of fatty acids, salts of acids of copra oil, optionally hydrogenated.

Among the amphoteric detergent surfactants optionally present in the composition according to the present invention, we may mention in particular alkylbetaines, alkylamidobetaines, sultaines, alkylamidoalkylsulfobetaines, derivatives of imidazolines, phosphobetaines, amphopolyacetates and amphopropionates.

Among the cationic detergent surfactants optionally present in the composition according to the present invention, we may mention in particular derivatives of quaternary ammonium.

Among the nonionic detergent surfactants optionally present in the composition according to the present invention, we may mention in particular alkyl polyglycosides, derivatives of castor oil, polysorbates, amides of copra, N-alkylamines.

As examples of fats of natural origin optionally present in the composition according to the present invention, we may mention saturated or unsaturated, linear or branched fatty alcohols of vegetable origin; saturated or unsaturated, linear or branched fatty acids of vegetable origin; esters of saturated or unsaturated, linear or branched fatty alcohols and fatty acids of vegetable origin, for example butyl stearate, cetyl palmitate, cetyl ricinoleate, decyl oleate, diisopropyl sebacate, diethylhexyl sebacate, ethyl linoleate, trilaurin, isocetyl stearate, isopropyl palmitate, isopropyl myristate, isostearyl isostearate, myristyl myristate, neopentylglycol diheptanoate, ethylhexyl cocoate, ethylhexyl hydroxystearate, ethylhexyl palmitate, ethylhexyl stearate, octyldodecyl myristate, pentaerylthrityl tetraisostearate, propylene glycol dicaprylate/dicaprate, stearyl caprylate, stearyl heptanoate, triisostearine, behenyl behenate, octyldodecyl stearoyl stearate, isocetyl stearoyl stearate, pentaerythrityl tetrabehenate, pentaerythrityl tetracaprylate/tetracaprate, dipentaerythrityl hexacaprylate/caprate; ethers of saturated or unsaturated, linear or branched fatty alcohols and fatty acids of vegetable origin; linear or branched alkanes of vegetable origin, for example phytosqualane; linear or branched alkenes of vegetable origin, for example phytosqualene; ethoxylated vegetable oils; ethoxylated methyl esters of vegetable origin; waxes of vegetable origin, for example carnauba wax, candelilla wax, cork fiber wax, sugar cane wax, and beeswax.

As examples of pigments optionally present in the composition according to the present invention, we may mention titanium dioxide, bismuth oxychloride, brown iron oxides, yellow iron oxides, black iron oxides, or red iron oxides or white or colored nacreous pigments such as titanium mica.

As sun filters optionally present in the composition according to the present invention, we may mention all those appearing in the cosmetic directive 76/768/EEC amended annex VII, and more particularly sunscreens of natural origin for example titanium oxide and zinc oxide.

The composition according to the present invention can be in the form of creams, milks, gel creams, fluid lotions, vaporizable fluid lotions. When the composition according to the present invention possesses appropriate fluidity characteristics, it can also serve for the impregnation of substrates consisting of synthetic or natural, woven or nonwoven textile fibers, or papers, for constituting articles, for example wipes, intended for care, protection or cleaning of the skin, of the scalp or of the hair, or for example papers for sanitary or household use.

The composition according to the present invention can be used by application on the skin, hair or scalp, whether it is direct application in the case of a cosmetic, dermocosmetic, dermo-pharmaceutical or pharmaceutical composition, or indirect application in the case of a product for the care, protection, or cleaning of the body, being in the form of a textile article, for example a wipe, or of paper, for example a paper for sanitary use, intended to be in contact with the skin, hair or scalp.

The invention also relates to the cosmetic use of the composition as defined above for cleaning, for protection and/or for care of the skin, hair or scalp.

The composition according to the present invention can be used for cleaning the skin, hair or scalp, and more particularly can be used as bath or shower gel, as shampoo. In this particular use, it further comprises at least one detergent surfactant as described above.

The composition according to the present invention can be used for care or for protection of the skin, for example as cream, as milk or as lotion for care or for protection of the face, hands and body.

The composition according to the present invention can also be used as a product for protecting the skin against the sun's rays, and as a skin make-up product.

According to another particular aspect, the invention relates to the cosmetic use of the composition as defined above and further comprising, per 100% of its weight, from 0.5 to 10 wt. % of dihydroxyacetone, for artificial bronzing and/or tanning of the skin.

The invention also relates to a method of cosmetic treatment for artificial bronzing and/or tanning of the skin, characterized in that it consists of applying, on the latter, the composition as defined above and further comprising per 100% of its weight, from 0.5 to 10 wt. % of dihydroxyacetone.

According to another aspect, the present invention relates to a method of preparation of the composition as defined above, comprising:

at least one step a) of mixing the fatty phase (P2) with the emulsifying system (A), as described above;

at least one step b) of emulsification of the mixture of the fatty phase (P2) and of the emulsifying system (A) obtained at the end of step a) with the aqueous phase (P1).

In the method according to the invention, the fatty phase (P2) comprises one or more vegetable oils based on monoglycerides and/or diglycerides and/or triglycerides, as defined above. In the case when the fatty phase (P2) does not consist of a single vegetable oil based on monoglycerides and/or diglycerides and/or triglycerides, the fatty phase (P2) is prepared by mixing its constituent ingredients at a temperature typically between 20° C. and 85° C., and even more particularly at a temperature between 20° C. and 60° C., and by means of any mixing device known by a person skilled in the art, for example by means of a mechanical stirring device equipped with an impeller of the "anchor" type, at stirring speeds between 50 rev/min and 500 rev/min, more particularly between 50 rev/min and 300 rev/min.

In the method according to the invention as described above, step a) of mixing the fatty phase (P2) with the emulsifying system (A) can advantageously be carried out at a temperature less than or equal to 90° C., more particularly at a temperature between 50° C. and 85° C., and even more particularly at a temperature between 60° C. and 85° C.

Step a) of mixing the fatty phase (P2) with the emulsifying system (A) of the method according to the invention can be carried out using any mixing device known by a person skilled in the art, for example by means of a mechanical stirring device equipped with an impeller of the "anchor" type, at stirring speeds between 50 rev/min and 500 rev/min, more particularly between 50 rev/min and 300 rev/min, and for example by means of a stirring device of the rotor-stator type at stirring speeds between 100 rev/min and 10 000 rev/min, more particularly between 500 rev/min and 4000 rev/min.

In the method according to the invention, step b) of emulsification of the mixture of the fatty phase (P2) and of the emulsifying system (A), as prepared at the end of step a), with the aqueous phase (P1) can advantageously be carried out at a temperature between 20° C. and 90° C., more particularly at a temperature between 50° C. and 85° C., and even more particularly at a temperature between 60° C. and 85° C.

In the method according to the invention, step b) of emulsification can be carried out using any mixing device known by a person skilled in the art, for example by means of a mechanical stirring device equipped with an impeller of the "anchor" type, at stirring speeds between 50 rev/min and 500 rev/min, more particularly between 50 rev/min and 300 rev/min, and for example by means of a stirring device of the rotor-stator type at stirring speeds between 100 rev/min and 10 000 rev/min, more particularly between 500 rev/min and 4000 rev/min.

In the method according to the invention as described above, the aqueous phase (P1) comprises water, and optionally one or more cosmetically acceptable organic solvents as described above, and at least one thickener and/or gelling agent of natural origin as described above. The aqueous phase (P1) is prepared by mixing water, and optionally one or more cosmetically acceptable organic solvents, with at least one thickener and/or gelling agent of natural origin as described above, at a temperature between 20° C. and 85° C., and even more particularly at a temperature between 20° C. and 60° C., and by means of any mixing device known by a person skilled in the art, for example by means of a mechanical stirring device equipped with an impeller of the "anchor" type, at stirring speeds between 50 rev/min and 500 rev/min, more particularly between 50 rev/min and 300 rev/min.

The following examples illustrate the invention, but without limiting it.

I—Preparation of Compositions in the Form of a Stable Oil-in-water Emulsion According to the Invention I-1—Preparation of an Emulsifying Composition (A1) Consisting of a Mixture of Reaction Products of Glucose and of 1,12-octadecanediol, and of 1,12-octadecanediol A glass reactor with a double jacket, in which a heat-transfer fluid circulates, and which is equipped with efficient stirring, is charged with 1074.6 g of 1,12-octadecanediol. The 1,12-octadecanediol is melted at a temperature of 90° C. in 30 minutes, and 100.3 g of anhydrous glucose is gradually dispersed in the reaction mixture and homogenized at 90° C. for 20 minutes. An acid catalytic system consisting of 1.50 g of 96% sulfuric acid is then added to the resultant mixture. The reaction mixture is then placed under a partial vacuum from 90 mbar to 25 mbar, and held at a temperature of 103° C.-106° C. for six hours with removal of the water formed by means of distillation apparatus. The reaction mixture is then cooled to 95° C.-100° C. and neutralized by adding 1.47 g of 30% soda, to adjust the pH of a 5% solution of this mixture to a value between 5.5 and 7.5. The composition (A1) thus obtained is then discharged.

The analytical characteristics of composition (A1) are as follows:
Appearance (visual): beige wax at room temperature;
pH of 5% solution: 7.3;
Melting point: 70.3° C.
Residual water content: 0.21%
Content of 1,12-octadecanediol: 81.4%
Content of 1,12-octadecanediol alkylpolyglucosides: 18.2%

I-2—Preparation of Stable Cosmetic Oil-in-water Emulsions

Emulsions (E1), (E'1), (E2), (E'2) and (E3) are prepared according to the same procedure given below:
the components of the fatty phase are introduced successively into a reactor and the resultant mixture is heated to a temperature of 80° C. while it is stirred at a speed of 80 rev/min by a stirrer equipped with an impeller of the anchor type;
the emulsifying system is then added to the fatty phase at a temperature of 80° C., and the mixture obtained is homogenized for 30 minutes by a stirrer equipped with an impeller of the anchor type, at a speed of 80 rev/min;
the aqueous phase comprising water, a preservative, a complexing agent (DISSOLVINE™GL-38) and a thickener (xanthan gum marketed under the name KELTROL™ CG T or a thickener based on acrylic copolymers marketed under the name CAPIGEL™98) is prepared separately by mixing its different ingredients at a temperature of 25° C. with mechanical stirring by a stirrer equipped with an impeller of the anchor type, at a speed of 80 rev/min;
the aqueous phase is then heated to a temperature of 80° C., stirred mechanically by a mechanical stirrer equipped with an anchor impeller at a speed of 80 rev/min, then added to the mixture comprising the fatty phase and the emulsifying system at a temperature of 80° C.;
the resultant mixture is sheared by means of an emulsifier of the rotor-stator type, marketed by the company SILVERSON, for 4 minutes at a speed of 4000 rev/min, then cooled to a temperature of 30° C., with mechanical stirring by a mechanical stirrer equipped with an anchor impeller at a speed of 80 rev/min under anchor for 10 minutes;
the preservative (GEOGARD™ 221) is then added to the emulsified mixture thus obtained, which is then cooled to room temperature and stirred for a further 10 minutes with a stirrer equipped with an impeller of the anchor type at a speed of 80 rev/min.

The compositions by weight of each of the emulsions are presented in Table 1 below.

TABLE 1

|  | (E1) | (E'1) | (E'2) | (E2) | (E3) |
|---|---|---|---|---|---|
| Emulsifying system |  |  |  |  |  |
| Composition (A1) | 4% | 4% | 4% | 0% | 0% |
| MONTANOV ™ 68[1] | 0% | 0% | 0% | 4% | 0% |
| ARLATONE ™ 2121[2] | 0% | 0% | 0% | 0% | 4% |
| Fatty phase |  |  |  |  |  |
| LANOL ™ 2681[3] | 10% | 10% | 10% | 10% | 10% |
| Sweet almond oil | 10% | 0% | 0% | 10% | 10% |
| Jojoba oil | 0% | 10% | 10% | 0% | 0% |
| DERMOFEEL ™ Toco 70[7] | 0.05% | 0.05% | 0.05% | 0.05% | 0.05% |
| Aqueous phase |  |  |  |  |  |
| GEOGARD ™ 221 [4] | 0.6% | 0.6% | 0.6% | 0.6% | 0.6% |
| DISSOLVINE ™GL-38 [5] | 0.3% | 0.3% | 0.3% | 0.3% | 0.3% |
| Citric acid | Q.s. pH = 5 | Q.s. pH = 5 | Q.s. pH = 5 | Q.s. pH = 5 | Q.s. pH = 5 |
| Water | Q.s. 100% | Q.s. 100% | Q.s. 100% | Q.s. 100% | Q.s. 100% |
| KELTROL ™ CG T[6] | 0.3% | 0% | 0.3% | 0.3% | 0.3% |
| CAPIGEL ™98[8] | 0% | 0.3% | 0% | 0% | 0% |

[1]Cetearyl glucoside/cetearyl alcohol mixture as described in WO 92/06778
[2]Sorbitan stearate/sucrose cocoate mixture
[3]Fatty ester (coco-caprylate caprate)
[4] Mixture of dehydroacetic acid and benzyl alcohol used as preservative
[5] Tetrasodium glutamate diacetate used as complexing agent
[6]Xanthan gum
[7]Mixture of tocopherols and *Helianthus annus* seed oil used as antioxidant
[8]Thickener based on acrylic copolymers The emulsions thus prepared are stored in an insulated climate chamber controlled to a temperature of 20° C. for 7 days. At the end of this period of 7 days, the appearance of each emulsion is observed and its viscosity is measured (Brookfield LVT, impeller 4, speed 6; in mPa·s). The emulsions are then replaced and stored in the same insulated climate chamber controlled to a temperature of 20° C. for 1 month. After a period of one month, each emulsion is taken out of the climate chamber for observation of its appearance.

The results of the observations and of the viscosity measurements obtained are shown in the following Table 2:

TABLE 2

|                              | (E1)             | (E'1)            | (E'2)            | (E2)             | (E3)             |
|------------------------------|------------------|------------------|------------------|------------------|------------------|
| Appearance at 7 days at 20° C. | Homogeneous    | Homogeneous     | Homogeneous     | Homogeneous     | Homogeneous     |
| Viscosity at 7 days at 20° C. | 30 000           | 30 000           | 31 000           | 27 000           | 20 000           |
| Appearance at 1 month at 20° C. | Homogeneous   | Homogeneous     | Homogeneous     | Homogeneous     | Homogeneous     |

These results show that the oil-in-water emulsion (E1) according to the invention remains homogeneous during storage at room temperature after a minimum time of one month, just like the oil-in-water emulsions (E'1), (E2), (E'2) and (E3) of the prior art.

II—Demonstration of the Improvement of the "Soaping" Effect of a Composition for Topical Use According to the Invention

II-1—Evaluation of the "Soaping" Effect

The "soaping" effect is reflected in the appearance of a whitish film on the surface of the skin when the composition is applied on the skin. It is evaluated experimentally by a suitably trained representative panel of users, according to the protocol presented in paragraph b) below.

a)—Principle of the Method

The "soaping" effect of a composition on the skin is evaluated during an operation of application on the skin by a panel of 11 people, suitably trained in said evaluation, who record the number of rotations made by the fingers applying the composition on the skin, starting from which a whitish film appears.

b)—Experimental Protocol

The surface of the testers skin, on which the composition to be evaluated will be applied, is cleaned beforehand with ethanol and then dried with absorbent paper. 50 µl of composition to be evaluated are taken using a micropipette and then deposited on the skin on the inside of the tester's wrist. The tester then makes rotations of about three centimeters with two fingers (index and middle finger) of the other hand with a frequency of about one rotation per second. The tester notes the number of rotations made until appearance of a whitish film on the surface of the skin on which the composition was applied.

c)—Expression of the Results

When the number of rotations required for appearance of a whitish film on the tester's skin is between 1 and 30, the composition tested is regarded as "soaping".

When the number of rotations required for appearance of a whitish film on the tester's skin is between 31 and 60, the composition tested is regarded as "slightly soaping".

When the number of rotations required for appearance of a whitish film on the tester's skin is greater than 61, the composition tested is regarded as "non-soaping".

For each composition tested, the arithmetic mean is calculated from the number of rotations recorded by each of the 11 testers, according to the following formula: Mean number of rotations=sum of the numbers of rotations of each tester/11.

II-2—Evaluation of the Consistency of a Composition

The consistency of a composition means the resistance to flow of said composition, which can be characterized by empirical observations, such as visual observation of the flow of the composition and/or by measuring a maximum force of compression applied by means of a texturometer equipped with a measuring probe and connected to data processing software.

II-2-1—Evaluation of the Consistency of the Composition by Visual Observation a)—Principle of the Method The consistency can be evaluated by visual observation of the flow of the composition being evaluated, which is contained in a bottle, after said bottle is rotated through 180°.

b)—Experimental Protocol

An amount of 50 grams of the test composition is put in a 100-ml clear glass bottle, which is closed by means of a threaded stopper. The suitably trained, experienced tester turns the bottle containing the test composition through 180° for 3 seconds and records his observation. He then rotates the bottle containing the test composition through 180° again.

c)—Expression of the Results

If, in the 3 seconds during which the bottle containing it is turned through 180°, the test composition flows spontaneously, the composition is described as "liquid" in use.

If, in the 3 seconds during which the bottle containing it is turned through 180°, the test composition does not flow spontaneously but flows following three manual impulses applied to the bottom of the bottle by the tester, the cosmetic composition is described as "pourable".

If, in the 3 seconds during which the bottle containing it is turned through 180°, the test composition does not flow spontaneously and if it does not flow following three manual impulses applied to the bottom of the bottle by the tester, the test composition is described as "compact".

II-2-2—Evaluation of the Consistency of a Composition by Measuring a Maximum Force of Compression a)—Principle of the Method The consistency can be evaluated by measuring a maximum force of compression, applied by means of a texturometer of model TEC95 marketed by the company ETIA, equipped with a hemispherical measuring probe connected to data processing software.

b)—Experimental Protocol

The test composition is put in a bottle with inside diameter of 7.7 centimeters and height of 4 centimeters, which after hermetic sealing is stored for 24 hours at a temperature of 20° C. The texturometer of model TEC95 consists of a translation unit on which a hemispherical probe made of stainless steel is mounted, which measures continuously, by means of a force sensor of 50 newton±0.025 newton, the force sustained by the sample by the sample during the movement of translation of the probe. The movement of translation of the probe consists of a simple movement of lowering of the probe in the sample. The speed of translation is set at 1 millimeter/second, the threshold for triggering measurement of the force sustained by the sample is 0.1 newton, and the depth of penetration of the probe into the sample is set at 10 millimeters. After this storage time of 24 hours, the bottle containing the composition to be tested is opened and is submitted to the experimental conditions stated below for measuring the maximum force of compression. During measurement, the variation of the forces is recorded by the ETIA software connected to the texturometer, which makes it possible to record a curve of the variation of the forces as a function of the duration of penetration and calculate, from this curve, the variation of the maximum force of compression expressed in newton.

c)—Expression of the Results

If the maximum force of compression, measured in the experimental conditions described above, is greater than or equal to a value of 0.3 newton, the test composition is regarded as "compact".

If the maximum force of compression, measured in the experimental conditions described above, is greater than or equal to a value of 0.2 newton and is definitely below a value of 0.3 newton, the test composition is regarded as "pourable".

If the maximum force of compression, measured in the experimental conditions described above, is definitely below a value of 0.2 newton, the test composition is regarded as "liquid".

II-3—Evaluation of the Criterion of Softness Imparted by a Composition

The criterion of softness imparted by a composition means the sensation of softness that the composition provides for the user when it is applied and spread on the skin.

a) Principle of the Method

The criterion of softness imparted by a composition is evaluated by determining a softness index following an operation of application of said composition on the skin by a panel of 11 people, suitably trained in said evaluation, who classify, on a scale ranging from 0 to 10, the sensation imparted by application of the test composition on the skin. A composition judged as "very soft" during its application will have a corresponding softness index of 10, and a composition judged as "not soft" or "rough" during its application on the skin will have a corresponding softness index of 0.

b) Experimental Protocol

The surface of the tester's skin on which the composition to be evaluated will be applied is cleaned beforehand with ethanol and then dried with absorbent paper. 50 µl of the composition to be evaluated is taken using a micropipette and then deposited on the skin on the inside of the tester's wrist. The tester then makes rotations of about three centimeters with two fingers (index and middle finger) of the other hand with a frequency of about one rotation per second.

The tester then characterizes the sensation of softness that he received on application of the test composition by ascribing a softness index on a scale ranging from 0 to 10.

c) Expression of the Results

For each composition tested, the arithmetic mean of the softness indices recorded by each of the 11 testers is calculated according to the following formula: mean softness index=sum of the softness indices of each tester/11.

II-4—Results Obtained for Emulsions (E1), (E'1), (E2), (E'2) and (E3)

The results of evaluation of the sensory properties of emulsion (E1) according to the invention and of emulsions (E'1), (E2), (E'2) and (E3) according to the prior art, namely the "soaping" effect, consistency and softness index, are presented in Table 3 below.

TABLE 3

|  | (E1) | (E'1) | (E'2) | (E2) | (E3) |
|---|---|---|---|---|---|
| | "Soaping" effect | | | | |
| Mean number of rotations | 87 | 56 | 70 | 9 | 16 |
| | Consistency | | | | |
| Visual observation | Compact | Compact | Pourable | Pourable | liquid |
| Maximum force of compression | 0.45 N | — | — | 0.5 N | 0.15 N |
| | Softness | | | | |
| Softness index | 9 | 4.4 | 5.5 | 9 | 6 |

Emulsion (E1) according to the invention and emulsions (E'1) and (E2) according to the prior art have a "compact" consistency whereas emulsion (E'2) has a "pourable" consistency and emulsion (E3) has a consistency judged as "liquid".

Emulsions (E1), (E2) and (E3) have a softness index above 5, whereas emulsions (E'1) and (E'2) have a softness index below 5.

Emulsions (E1) and (E2) have a softness index above 7, in contrast to emulsions (E'1), (E'2) and (E3), which have a softness index of 4.4, 5.5 and 6.0, respectively.

However, emulsions (E2) and (E3) of the prior art are characterized by a considerable soaping effect, as the average number of rotations required for appearance of a whitish film on the skin is 9 and 16 respectively, whereas emulsion (E1) is classified as "non-soaping" according to the protocol employed as the average number of rotations required for appearance of a whitish film on the skin is 87. Emulsion (E'1) according to the prior art is classified as "slightly soaping" according to the protocol employed as the average number of rotations required for appearance of a whitish film is 56, and therefore it does not meet the requirement for this specific property.

Emulsion (E'2), which only differs from emulsion (E1) according to the invention in the nature of the fatty phase (emulsion (E1) comprises sweet almond oil and emulsion (E'2) comprises jojoba oil), shows a satisfactory "non-soaping" effect, but a consistency and a softness index that do not satisfy the requirements.

The composition according to the invention (E1) therefore has improved sensory properties relative to emulsions (E'1), (E2), (E'2) and (E3) of the prior art.

III—Demonstration of the Improvement of Sensory Properties of a Self-tanning Oil-in-water Emulsion

III-1—Preparation of Self-tanning Oil-in-water Emulsions

Three self-tanning oil-in-water emulsions (E4), (E5), (E6) are prepared according to the same procedure, as follows:

Emulsions (E4), (E5) and (E6) are prepared using the following procedure:

The components of the fatty phase are introduced successively into a reactor and are homogenized at a temperature of 80° C. for 15 minutes with a stirrer equipped with an impeller of the "anchor" type at a stirring speed of 80 rev/min.

The emulsifying system is then added to the fatty phase at a temperature of 80° C., and the mixture thus obtained is homogenized for 30 minutes using a mechanical stirrer equipped with an impeller of the anchor type, at a speed of 80 rev/min.

The aqueous phase comprising water, glycerol, propylene glycol and polymer thickener (KELTROL™ CG T) is prepared separately by mixing its various constituents in a beaker at a temperature of 25° C. with mechanical stirring by a stirrer equipped with an impeller of the "anchor" type at a speed of 80 rev/min. Said aqueous phase is then heated to a temperature of 80° C. and maintained at this temperature for 15 minutes, with stirring.

The aqueous phase is then added to the mixture comprising the fatty phase and the emulsifier at a temperature of 80° C.

The resultant mixture is then sheared by means of an emulsifier of the "rotor-stator" type, marketed by the company SILVERSON, for 4 minutes at a speed of 4000 rev/min, at a temperature of 80° C.

The emulsion obtained is then stirred for 30 minutes with a stirrer equipped with an impeller of the "anchor" type at a stirring speed of 100 rev/min, and is then left to cool.

When the temperature reaches 40° C., the solution of 50% dihydroxyacetone in water is added as well as the preservative GEOGARD™ 221. When the temperature reaches 20° C., the emulsion obtained is stirred for 15 minutes with a stirrer equipped with an impeller of the "anchor" type at a stirring speed of 100 rev/min.

The compositions by weight of each emulsion are presented in Table 4 below.

TABLE 4

|  | (E4) | (E5) | (E6) |
|---|---|---|---|
| Emulsifying system |  |  |  |
| Composition (A1) | 2% | 0% | 0% |
| MONTANOV ™ 68[1] | 0% | 2% | 0% |
| MONTANOV ™ 202[9] | 0% | 0% | 2% |
| Fatty phase |  |  |  |
| Triglyceride C8-C10 | 15% | 15% | 15% |
| DERMOFEEL ™ Toco 70[7] | 0.05% | 0.05% | 0.05% |
| Aqueous phase |  |  |  |
| GEOGARD ™ 221 [4] | 0.6% | 0.6% | 0.6% |
| Glycerol | 3% | 3% | 3% |
| Propylene glycol | 2% | 2% | 2% |
| Water | Q.s. 100% | Q.s. 100% | Q.s. 100% |
| KELTROL ™ CG T[6] | 0.2% | 0.2% | 0.2% |
| Self-tanning agent |  |  |  |
| Dihydroxyacetone in solution at 50% in water | 10% | 10% | 10% |

[9]Emulsifying composition (arachidyl glucoside, arachidyl alcohol + behenyl alcohol).

III-2—Evaluation of the Properties of the Self-tanning Oil-in-water Emulsions (E4), (E5) and (E6)

Emulsions (E4), (E5) and (E6) thus prepared are then stored in an insulated climate chamber controlled to a temperature of 20° C. for 7 days. At the end of this period of 7 days, the appearance of each emulsion prepared is observed and the viscosity of each emulsion is measured. The emulsions are then replaced and stored in the same insulated climate chamber controlled to a temperature of 20° C. for 1 month. After a period of one month, each emulsion is taken out of the climate chamber for observation of its appearance.

Emulsions (E4), (E5) and (E6) are characterized by:
evaluation of their sensory properties according to the protocols described in paragraphs II-1, II-2 and II-3 of the present application;
observation of their visual appearance after storing for three months at a temperature of 20° C.;
observation of their visual appearance after storing for three months at a temperature of 45° C.

The results obtained are shown in Table 5 below:

TABLE 5

|  | (E4) | (E5) | (E6) |
|---|---|---|---|
|  | "Soaping" effect | | |
| Average number of rotations | 94 | 13 | 18 |
|  | Consistency | | |
| Visual observation | Compact | Compact | Pourable |
| Maximum force of compression | 0.3 N | 0.35 N | 0.2 N |
|  | Softness | | |
| Softness index | 9 | 9 | 8 |

The self-tanning emulsions (E5) and (E6) of the prior art are characterized by a softness index of 9 and 8 respectively, and by a consistency evaluated as "compact" and "pourable", respectively.

However, the self-tanning emulsions (E5) and (E6) of the prior art are characterized by a considerable soaping effect, as the average number of rotations required for appearance of a whitish film on the skin is 13 and 18, respectively.

The self-tanning emulsion (E4) according to the invention is classified as "non-soaping" according to the protocol employed, as the average number of rotations required for appearance of a whitish film on the skin is 94.

Moreover, the self-tanning emulsion (E4) according to the invention is characterized by a softness index of 9, and by a consistency judged as "compact".

Consequently, the self-tanning emulsion (E4) according to the invention has improved sensory properties relative to those imparted by emulsions (E5) and (E6) of the prior art.

IV—Formulations

In the following formulas, the percentages are expressed as percentage by weight per 100% of the weight of the formulation.

Example IV-1

"Day Fluid" Formulation

| | Formula | |
|---|---|---|
| A | Composition (A1) | 3.00% |
|  | MONTANOV ™ 14 | 1.50% |
|  | DUB ™ BB | 2.00% |
|  | Butyrospermum Parkj (Bio) | 1.50% |
|  | DUB ™MUG | 1.50% |
|  | Squalane | 3.00% |
|  | Caprylic/capric triglyceride | 6.00% |
|  | DUB ™ISIP | 3.00% |
|  | DERMOFEEL ™ Toco 70 | 0.10% |

-continued

| | Formula | |
|---|---|---|
| B | Water | Q.S. 100.00% |
| | Aqueous *Hordeum Vulgare* extract | 3.50% |
| | Xantham Gum | 0.60% |
| C | GEOGARD ™ 221 | 0.60% |
| | AQUAXYL ™ | 3.00% |
| | DERMOSOFT ™ 700 | 0.50% |
| | Soda | Q.S. pH = 5.5 |

Procedure: phase B is added to phase A at a temperature of 80° C., with stirring with a turbine of the rotor/stator type, then cooled with moderate stirring with a mechanical stirrer equipped with a stirring impeller of the anchor type at a speed of 80 rev/min. Phase C is then added in the same conditions of stirring at a temperature of 40° C.

Example IV-2

Dermopurifying Makeup-removal Milk

| | Formula | |
|---|---|---|
| A | Water | Q.S. 100.00% |
| | Amigum (Sclerotium gum) | 0.15% |
| B | Water | Q.S. 30.00% |
| | LIPACIDE ™C8G | 1.00% |
| | Soda at 48% | Q.S. pH = 5.5 |
| | PROTEOL ™OAT | 2.00% |
| | Glycerol | 2.00% |
| C | Composition (A1) | 4.00% |
| | Caprylic/capric triglyceride | 4.00% |
| | Squalane | 4.00% |
| | *Corylus Nucifera* (Hazel) seed oil | 2.00% |
| | *Prunus Amygdalus Dulcis* (Sweet almond) oil | 2.00% |
| | Beeswax | 0.30% |
| D | Aqueous *Hordeum Vulgare* extract | 10.00% |
| | GEOGARD ™ 221 | 0.60% |
| | DERMOFEEL ™ Toco 70 | 0.10% |

Procedure: phases A and B are prepared separately beforehand, then phase A is added to phase B at a temperature of 80° C. with mechanical stirring with a stirrer equipped with an impeller of the anchor type at a speed of 80 rev/min. Phase C is then added to the mixture of phase A+B at a temperature of 80° C. with stirring with a rotor/stator turbine and is then cooled with moderate stirring. Phase D is then added at 40° C.

Example IV-3

Intense Firmness Body Milk

| | Formula | |
|---|---|---|
| A | Water | Q.S. 100.00% |
| | Soda at 48% | Q.S. pH = 5.5 |
| | AVICEL ™PC 611 | 0.40% |
| | Glycerol | 2.00% |

-continued

| | Formula | |
|---|---|---|
| B | Composition (A1) | 2.00% |
| | DUB ™ISIP | 4.00% |
| | Caprylic/capric triglyceride | 7.00% |
| | *Carthamus Tinctorius* (Safflower) oil | 1.00% |
| | SEPILIFT ™DPHP | 1.00% |
| C | Aqueous *Hordeum Vulgare* extract | 10.00% |
| D | GEOGARD ™ 221 | 0.60% |
| | DERMOFEEL ™ Toco 70 | 0.10% |
| | Fragrance | 0.10% |

Procedure: phase A is added to phase B at 80° C. with stirring with a rotor/stator turbine. The mixture obtained is then cooled to a temperature of 40° C. with moderate stirring using a mechanical stirrer equipped with an impeller of the anchor type at a speed of 80 rev/min. Phase C is then added at 40° C., then phase D is added at 40° C.

MONTANOV™ 14 is a mixture of myristic alcohol and myristyl polyglucosides marketed by the company SEPPIC as emulsifier.

DUB™ BB is behenyl behenate marketed by the company STEARINERIE DUBOIS.

DUB™MUG is glycerol undecylenate marketed by the company STEARINERIE DUBOIS.

DUB™ISIP is isopropyl isostearate marketed by the company STEARINERIE DUBOIS.

DERMOFEEL™ Toco 70 is a mixture of tocopherols and Helianthus Annus seed oil used as antioxidant and marketed by the company Dr Straetmans.

GEOGARD™ 221 is a mixture of dehydroacetic acid and benzyl alcohol used as preservative and marketed by the company LONZA.

LIPACIDE™C8G is capryloyl glycine marketed by the company SEPPIC as dermopurifying active agent.

PROTEOL™OAT is a mixture of N-lauryl amino acids obtained by full hydrolysis of oat protein as described in WO 94/26694 and marketed by the company SEPPIC.

AVICEL™PC 611 is microcrystalline cellulose marketed by the company FMC.

SEPILIFT™DPHP is DiPalmitoylHydroxyProline marketed by the company SEPPIC as antiwrinkle active ingredient.

The invention claimed is:

1. A composition that is in the form of an oil-in-water emulsion comprising per 100% of weight of the composition:
    a)—From 0.1 to 10 wt. % of an emulsifying system (A) consisting per 100% of weight of said emulsifying system (A):
    (i)—From 5 to 95 wt. % of a mixture of reaction products of a reducing sugar and of 1,12-octadecanediol, said mixture of reaction products consisting essentially of hydroxyoctadecyl polyglycosides of formula (I):

$$HO-R-O-(G)_n-H \qquad (I)$$

and of polyglycosyloctadecyl polyglycosides of formula (II):

$$H-(G)_m-O-R-O-(G)_p-H \qquad (II),$$

where, in formulas (I) and (II), G represents the residue of said reducing sugar and R represents the 1,12-octadecane-diyl divalent radical and where n, m and p, which may be identical or different, each represent, independently of one another, a decimal number between 1 and 5; and (ii)—From 95 to 5 wt. % of 1,12-octadecanediol;

b)—From 0.6 to 5 wt. % of at least one thickener and/or gelling agent selected from thickeners and/or gelling agents of natural origin selected from the elements of a group consisting of xanthan gum, acacia gum, guar gum, carob, fenugreek, carraghenates, alginates and galactomannans;

c)—From 10 to 50 wt. % of a fatty phase (P2) consisting of one or more vegetable oils based on monoglycerides and/or diglycerides and/or triglycerides; and d)—From 89.89 to 35 wt. % of a cosmetically acceptable aqueous phase (P1).

2. The composition as claimed in claim 1, further comprising, per 100% of the weight of the composition, from 0.5 to 10 wt. % of dihydroxyacetone.

3. A method for cleaning the skin, hair or scalp of an individual, which comprises treating the skin, hair or scalp of said individual with an effective amount of the composition of claim 1.

4. A method for artificial tanning the skin of an individual, which comprises applying to the skin of said individual an effective amount of the composition of claim 2.

5. A method of cosmetic treatment for artificial tanning of the skin, characterized in that the composition as claimed in claim 2 is applied on the skin.

6. A method of preparation of the composition as defined in claim 1, comprising:

at least one step a) of mixing the fatty phase (P2) with the emulsifying system (A); and at least one step b) of emulsification of the mixture of the fatty phase (P2) and of the emulsifying system (A) obtained at the end of step a) with the aqueous phase (P1).

\* \* \* \* \*